United States Patent [19]

Kurata

[11] 4,047,563
[45] Sept. 13, 1977

[54] HEAT EXCHANGER FOR ARTIFICIAL HEART AND LUNG DEVICES

[75] Inventor: Motoji Kurata, Hatsukaichi, Japan

[73] Assignee: Japan Medical Supply Co., Ltd., Horishima, Japan

[21] Appl. No.: 678,373

[22] Filed: Apr. 19, 1976

[30] Foreign Application Priority Data

Jan. 27, 1976 Japan .................... 51-7192[U]

[51] Int. Cl.² .............. F28F 9/02; F28F 21/06; A61M 1/03; A61F 7/00
[52] U.S. Cl. .............. 165/158; 23/258.5 A; 128/400; 165/DIG. 22
[58] Field of Search ........... 23/258.5 BH, 258.5 MH, 23/258.5 R, 258.5 A; 165/DIG. 22, 158; 128/400

[56] References Cited

U.S. PATENT DOCUMENTS

| | | | |
|---|---|---|---|
| 3,254,707 | 6/1966 | Ferguson | 165/DIG. 22 |
| 3,256,883 | 6/1966 | DeWall | 23/258.5 BH |
| 3,468,631 | 9/1969 | Raible et al. | 23/258.5 BH |
| 3,521,706 | 7/1970 | Schaefer et al. | 165/158 X |
| 3,804,161 | 4/1974 | Nowak | 165/158 |

OTHER PUBLICATIONS

Esmond et al., "Profound Hypothermia - High Efficiency", *J. of Thoracic & Cardia, Surg.*, vol. 42, No. 5, Nov. 1961, pp. 563-574.

*Primary Examiner*—Barry S. Richman
*Attorney, Agent, or Firm*—Armstrong, Nikaido & Marmelstein

[57] ABSTRACT

A heat exchanger is provided for use in artificial heart and lung devices which comprises a tubular shell having inlet and outlet ports for a heating medium, a great number of elongated tubes arranged in parallel axially within the tubular shell, a pair of fixing plates located at both ends of the tubular shell for fixedly securing the elongated tubes within the tubular shell, a cap on the inlet side having an inlet port for blood and being adapted to be secured at one end of the tubular shell, another cap on the outlet side having an outlet port for blood and an air bubble remover for removing air bubble contained in the blood flowing therethrough and being adapted to be secured at the other end of the tubular shell.

4 Claims, 2 Drawing Figures

HEAT EXCHANGER FOR ARTIFICIAL HEART AND LUNG DEVICES

BACKGROUND OF THE INVENTION

This invention relates to a heat exchanger for use with artificial heart and lung devices.

In the case of circulating the blood of a patient through an artificial heart and lung device in a surgical operation on his heart, the temperature of the blood generally tends to drop while it is circulated through the circuit outside the patient's body because the temperature in the operation room is lower than the body temperature thereof. In order to heat the blood to the body temperature again and return it to the patient's body, it is essential to provide a heat exchanger.

As for heat exchangers for use with artificial heart and lung devices, there have heretofore been employed two types. One type includes one length of a blood transport tube within a tubular shell, and the other type includes a spiral blood transport tube mounted within a tubular shell in which a heating medium is introduced to heat the blood. These devices are, however, disadvantageous in that since the surface area through which the blood can receive the heat from the heating medium is small, the heat exchanging efficiency obtainable thereby is low. In order to eliminate the above-mentioned disadvantage, the applicant of the present invention devised and filed a Japanese Utility Model Application No. 119,356/1947 in which a large number of elongated tubes are mounted in parallel within a tubular shell to improve the heat exchanger efficiency. This device can provide a high heat exchanging efficiency since the surface area through which the blood can receive the heat from the heating medium is large, and can be put satisfactorily into practical use. However, it has a room left to be improved, because it is not provided with means for removing air bubbles produced in the blood.

In artificial heart and lung devices, it is necessary to add some amount of oxygen to the blood passing therethrough by spraying oxygen to the blood. Therefore, the passage of the blood oversaturated with oxygen inside the heat exchanger allows the oxygen in the blood to expand by heating thereby producing oxygen bubbles. Conventional devices are disadvantageous in that since they are not provided with means for removing such air bubbles, it is absolutely necessary for a doctor to frequently remove the air bubbles to avoid complications resulting from the bubbles.

SUMMARY OF THE INVENTION

Therefore, the object of the present invention is to provide a heat exchanger for use with artificial heart and lung devices having an improved heat exchanging efficiency by providing a bubble remover for removing air bubbles produced in the blood during the operation.

The present invention is characterized in that a large number of elongated tubes through which the blood is allowed to flow are arranged in parallel within a tubular shell, and the space on the side of the outlet for receiving the blood is divided into an inner chamber and an outer chamber by a baffle plate so that the blood can first be accumulated in the inner chamber to remove air bubbles in the blood, and then circulated in outer chamber thereby enabling the blood free of air bubbles to be introduced into the patient's body.

The present invention is advantageous in that it can provide a high heat exchanging efficiency, and also oversaturated oxygen in the form of air bubbles in the blood can be substantially removed. Further, the present invention is advantageous in that it can provide a disposable heat exchanger of a simple arrangement in place of conventional devices which require considerable manpower for flushing, assembly operation and sterilization etc., for each repeated use.

Other objects, features and advantages of the present invention will be readily apparent from the following description taken in conjunction with the accompanying drawing.

DETAILED DECRIPTION OF THE PREFERRED EMBODIMENT

Figure 1:
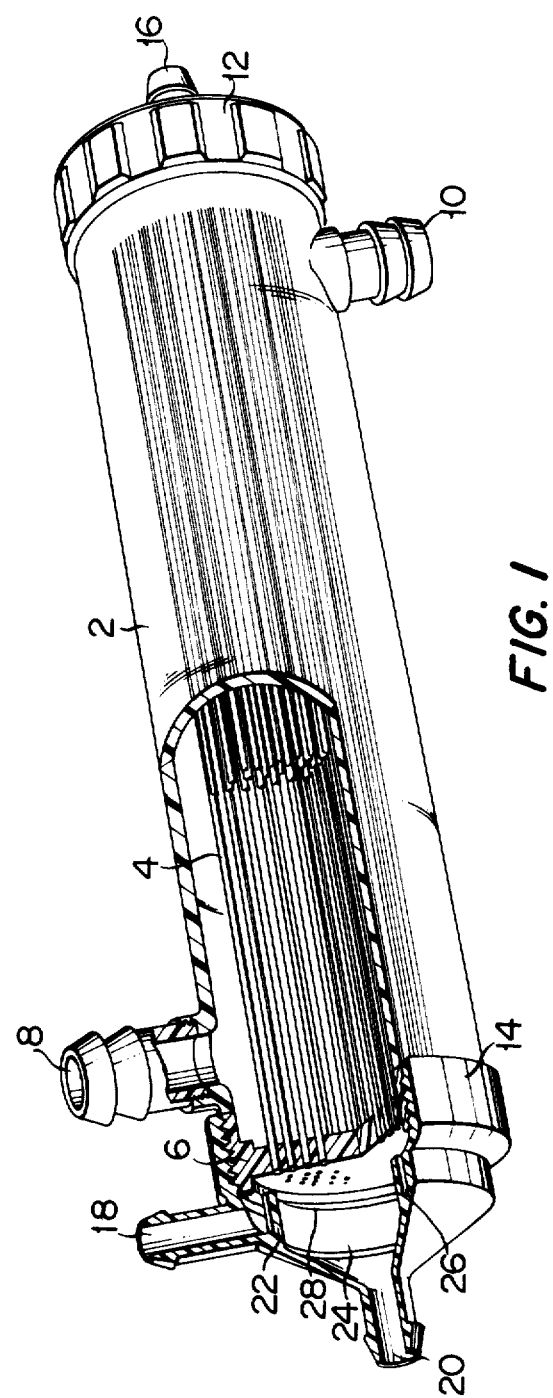
FIG. 1 is a partially cut-away perspective view of the present invention.
Figure 2:
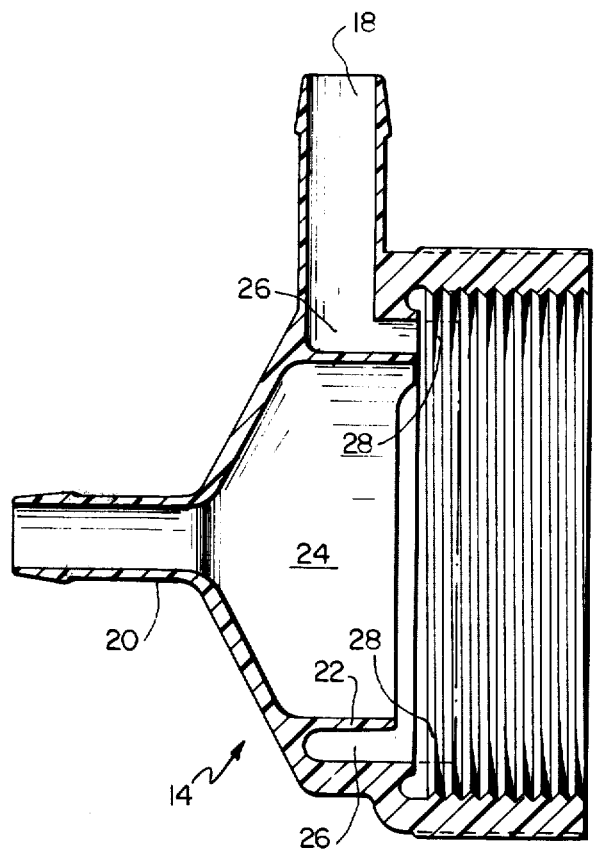
FIG. 2 is a cross-section view of outlet side cap of the present invention.

In the drawing, reference numeral 2 denotes a tubular shell formed by a synthetic resin such as acrylic resin etc. It is preferable to form the tubular shell with a transparent synthetic resin, however, it is not limited thereto. The tubular shell may be made of a metal or glass etc.

Within the tubular shell 2, there are mounted in parallel a great number of elongated tubes 4 through which the blood is allowed to flow. The bundle, consisting of the elongated tubes 4 arranged in a parallel relationship with the tubular shell, is fixedly secured by a pair of fixing plates at both ends thereof. The elongated tubes 4 are preferably made of, for example, a metal such as stainless steel etc., however, they are now always limited thereto. A synthetic resin having a good workability and which does not react with the blood can also be used for the material to form the tubes 4.

Reference numeral 8 represents an inlet port for a heating medium, which flows inside the tubular shell 2 to heat the blood flowing within the elongated tubes 4 and then flows out through an outlet port 10. The pair of fixing plates 6 may be formed as integral parts of the tubular shell 2, or alternatively the two may be separately manufactured and then permitted to adhere as integral parts thereof to each other by means of an adhesive. In the embodiment shown in the drawing, the fixing plates 6 have screw threads on the upper peripheral surface thereof which are engageable with the screw threads on the inner surfaces of caps 12 and 14 located at both ends thereof. It is essential to ensure liquid-tightness between the fixing plates 6 and the caps 12 and 14 to prevent leakage of the blood therethrough. In order to maintain liquid-tightness, seal members such as "O" rings etc., may be interposed between the fixing plates and the caps though not shown in the drawing.

The cap 12 on the inlet side has an inlet port 16 for blood, and the cap 14 on the outlet side has an outlet port 18 and an air bubble remover 20. The cap 14 on the outlet side has an interior space which is divided by an annular baffle plate 22 into an inner chamber 24 and an outer chamber 26. A proper clearance 28 is provided between the annular baffle plate 22 and the fixing plate 6 so that the blood can flow from the inner chamber 24 into the outer chamber 26. Though not shown in the drawing, one end of a rubber tube is inserted in the air bubble remover 20, and the other end of which is closed.

Thus, the blood flows through the inlet port 16 into the elongated tubes 4. A heating medium is allowed to flow through the inlet port 8 into the tubular shell 2 so as to exchange the heat with blood within the elongated tubes 4, and then flows out through the outlet port 10. In a practical application, this heat exchanger is used with the air bubble remover 20 disposed in upright position. The blood flowing inside the elongated tubes 4 effects heat exchange with the heating medium flowing in the tubular shell, and then flows into the inner chamber 24 defined inside the cap 14 on the outlet side. The oversaturated oxygen in the blood forms air bubbles and passes through the air bubble remover 20 into a rubber tube not shown in the drawing, because the air bubble remover is located in the upright position. The oversaturated oxygen can thus be changed into air bubbles and removed from the blood flowing through the heat exchanger. Because of the other end of the rubber tube being closed as mentioned above, air bubbles will accumulate inside the rubber tube. As a result the blood is pushed downwards by the action of the accumulated air bubbles and is allowed to pass through the space 28 defined between the annular baffle plate 22 and the fixing plate 6 so that the blood free of air bubbles can flow from the inner chamber 24 into the outer chamber 26. The blood which flowed into the outer chamber 26 will flow out through the outlet port 18.

It is to be understood that the above description is by way of example only, and that the details for carrying the invention into effect may be varied without departing from the scope of the invention claimed.

What is claimed is:

1. A heat exchanger for use in artificial heart and lung devices, comprising a tubular shell having an inlet side and an outlet side for a heating medium; a plurality of elongated tubes arranged in parallel axially within said tubular shell; a pair of fixing plates locates at both ends of the tubular shell; a first cap secured to the inlet side of said tubular shell having an inlet port for blood; a second cap secured to the outlet side of said tubular shell having an outlet port for blood and air bubble remover means, said air bubble remover means being positioned vertically above said outlet port and downstream thereof relative to the direction of the flow of blood; and an annular baffle means secured within said second cap to divide the inside of said second cap into an inner chamber and an outer chamber, said blood outlet port communicating with said outer chamber and said air bubble remover means communicating with said inner chamber, wherein said annular baffle means accumulates the blood once in the inner chamber so as to remove air bubbles therefrom through the air bubble remover means and then allows the blood to flow into the outer chamber and subsequently to flow out through the outlet port.

2. A heat exchanger as defined in claim 1, wherein said tubular shell is made of a transparent synthetic resin and said plurality of elongated tubes are made of metal.

3. A heat exchanger as defined in claim 1 wherein said bubble remover means comprises a port in said second cap, and a tube having one end connected to said port and the other end being closed.

4. A heat exchanger as defined in claim 1 wherein said second cap comprises a first annular portion coupled to said tubular shell; a second annular portion coupled to said first annular portion and a truncated conical portion coupled to said second annular portion wherein said first annular portion, said second annular portion and said conical portion are all axially aligned and wherein said annular baffle means is coupled to said conical portion such that said outer chamber is formed between said second annular portion and said baffle means.

* * * * *